United States Patent
Levenberg et al.

(10) Patent No.: US 9,718,057 B2
(45) Date of Patent: Aug. 1, 2017

(54) MICROFLUIDIC DEVICE AND METHOD THEREOF

(71) Applicant: Technion Research and Development Foundation LTD., Haifa (IL)

(72) Inventors: Shulamit Levenberg, Haifa (IL); Jonathan Shemesh, Sydney (AU)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 120 days.

(21) Appl. No.: 14/760,589

(22) PCT Filed: Jan. 15, 2014

(86) PCT No.: PCT/IL2014/050041
§ 371 (c)(1),
(2) Date: Jul. 13, 2015

(87) PCT Pub. No.: WO2014/111928
PCT Pub. Date: Jul. 24, 2014

(65) Prior Publication Data
US 2015/0352552 A1    Dec. 10, 2015

Related U.S. Application Data

(60) Provisional application No. 61/753,441, filed on Jan. 17, 2013, provisional application No. 61/826,734, filed on May 23, 2013.

(51) Int. Cl.
*B01L 3/00* (2006.01)
*G01N 1/30* (2006.01)
(Continued)

(52) U.S. Cl.
CPC ....... *B01L 3/502723* (2013.01); *B01L 3/5027* (2013.01); *G01N 1/30* (2013.01);
(Continued)

(58) Field of Classification Search
CPC ..... B01L 2200/0605; B01L 2200/0673; B01L 2200/0694; B01L 2200/16;
(Continued)

(56) References Cited

U.S. PATENT DOCUMENTS

2002/0195463 A1   12/2002   Seki et al.
2005/0130226 A1    6/2005   Ahn et al.
(Continued)

FOREIGN PATENT DOCUMENTS

WO    WO99/46045       9/1999
WO    WO03/035229      5/2003
WO    WO2005/070546    8/2005

OTHER PUBLICATIONS

Shemesh et al. PNAS, vol. 111, No. 31, Aug. 5, 2014, pp. 11293-11298.*
(Continued)

*Primary Examiner* — Maureen Wallenhorst
(74) *Attorney, Agent, or Firm* — Pearl Cohen Zedek Latzer Baratz LLP

(57) ABSTRACT

A microfluidic device includes a platform with a microstructure. The microstructure include a primary channel and a plurality of chambers that open to the primary channel to enable a sample fluid that is loaded into the device via the primary channel to flow into the chambers. Each chamber has a volume that is less than tens of nanoliters and is connected by a vent to a secondary channel of the microstructure. A width of the vent is configured to enable a gas to escape from the chamber to the secondary channel while inhibiting flow of the sample fluid from the chamber into the secondary channel.

19 Claims, 9 Drawing Sheets

(51) Int. Cl.
*G01N 1/18* (2006.01)
*C40B 50/00* (2006.01)

(52) U.S. Cl.
CPC ............. *B01L 2200/0605* (2013.01); *B01L 2200/0673* (2013.01); *B01L 2200/0694* (2013.01); *B01L 2200/16* (2013.01); *B01L 2300/048* (2013.01); *B01L 2300/0816* (2013.01); *B01L 2300/0864* (2013.01); *B01L 2300/0896* (2013.01); *B01L 2300/12* (2013.01); *B01L 2400/0406* (2013.01); *G01N 1/18* (2013.01); *Y10T 436/2575* (2015.01)

(58) Field of Classification Search
CPC ....... B01L 2300/048; B01L 2300/0816; B01L 2300/0864; B01L 2300/0896; B01L 2300/12; B01L 2400/0406; B01L 3/5027; B01L 3/502723; G01N 1/18; G01N 1/30; Y10T 436/25; Y10T 436/2575

USPC ........ 436/174, 180; 422/502, 503, 504, 505, 422/507; 435/30, 309.1
See application file for complete search history.

(56) References Cited

U.S. PATENT DOCUMENTS

| | | | |
|---|---|---|---|
| 2007/0280857 A1* | 12/2007 | Song | B01L 3/502723 422/400 |
| 2011/0003372 A1 | 1/2011 | Jeon et al. | |
| 2011/0143964 A1 | 6/2011 | Zhou et al. | |
| 2013/0053252 A1* | 2/2013 | Xie | C12Q 1/6874 506/2 |

OTHER PUBLICATIONS

Supplementary European Search Report for EP Application No. 14740619 dated May 11, 2016.

* cited by examiner

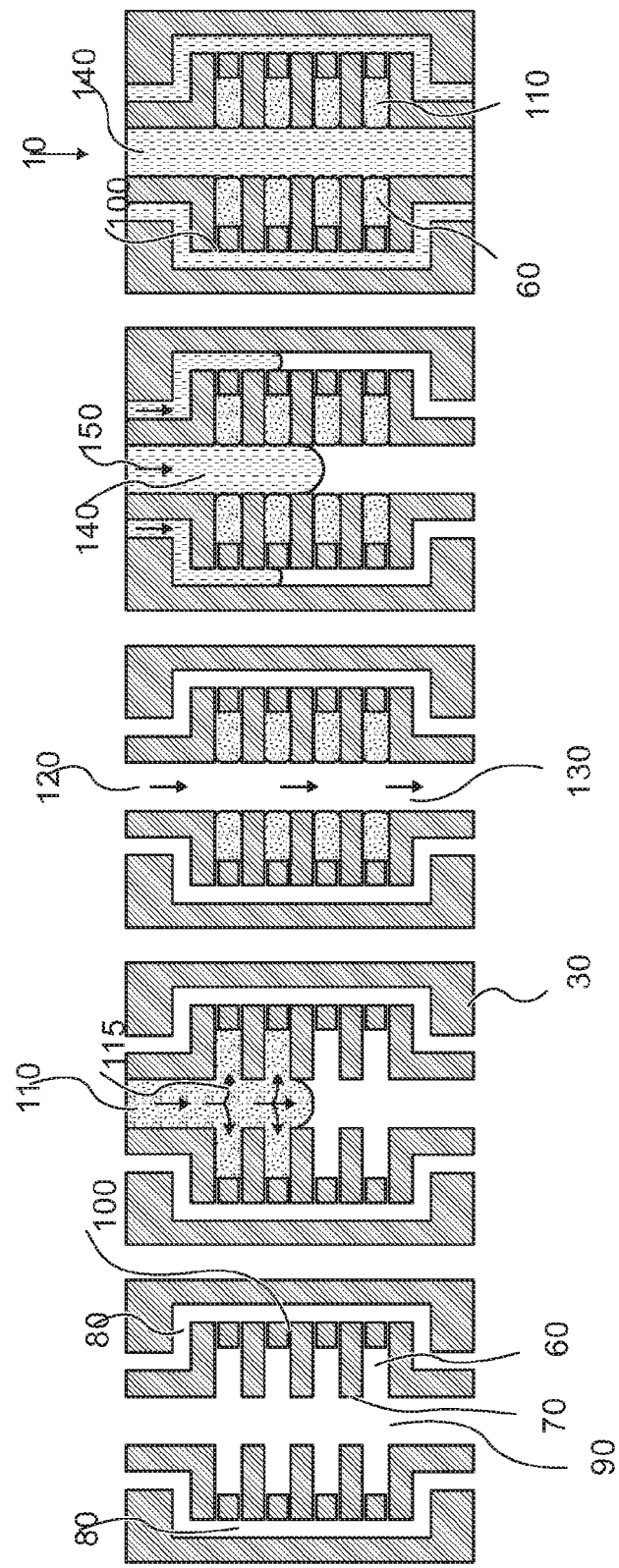

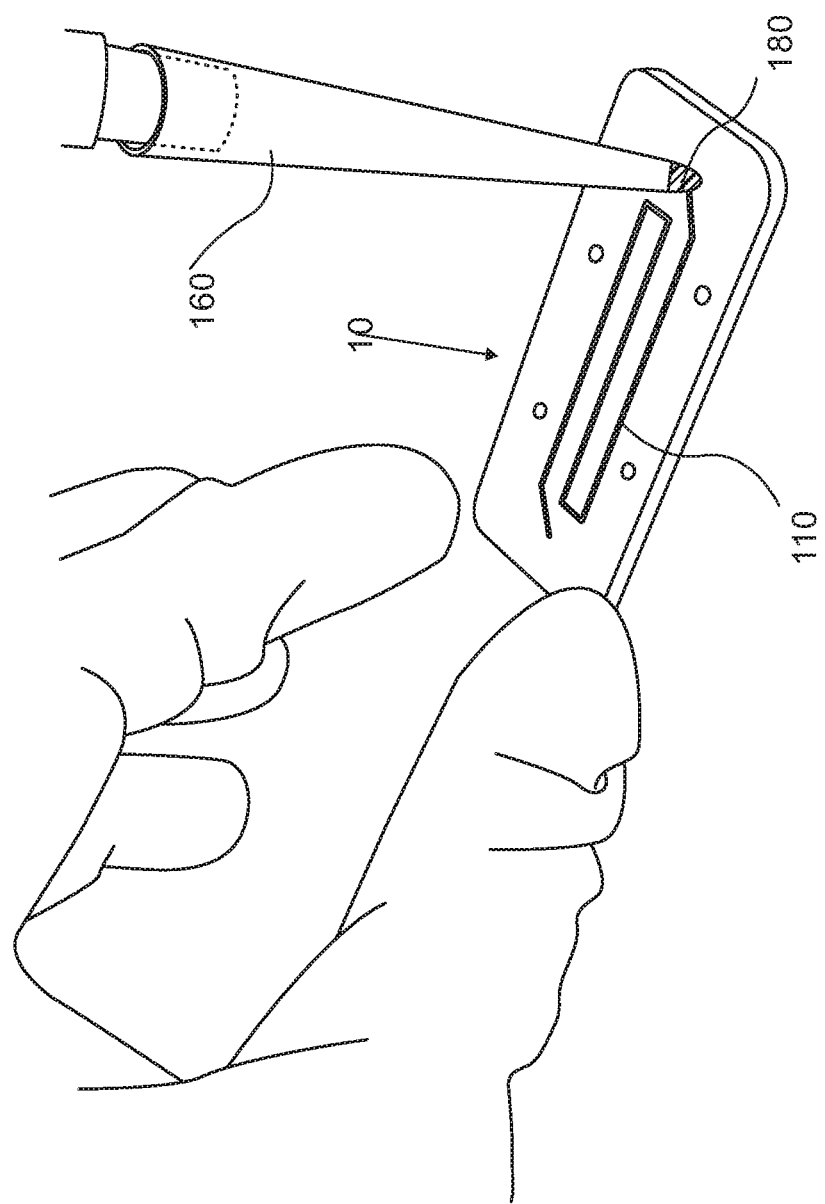

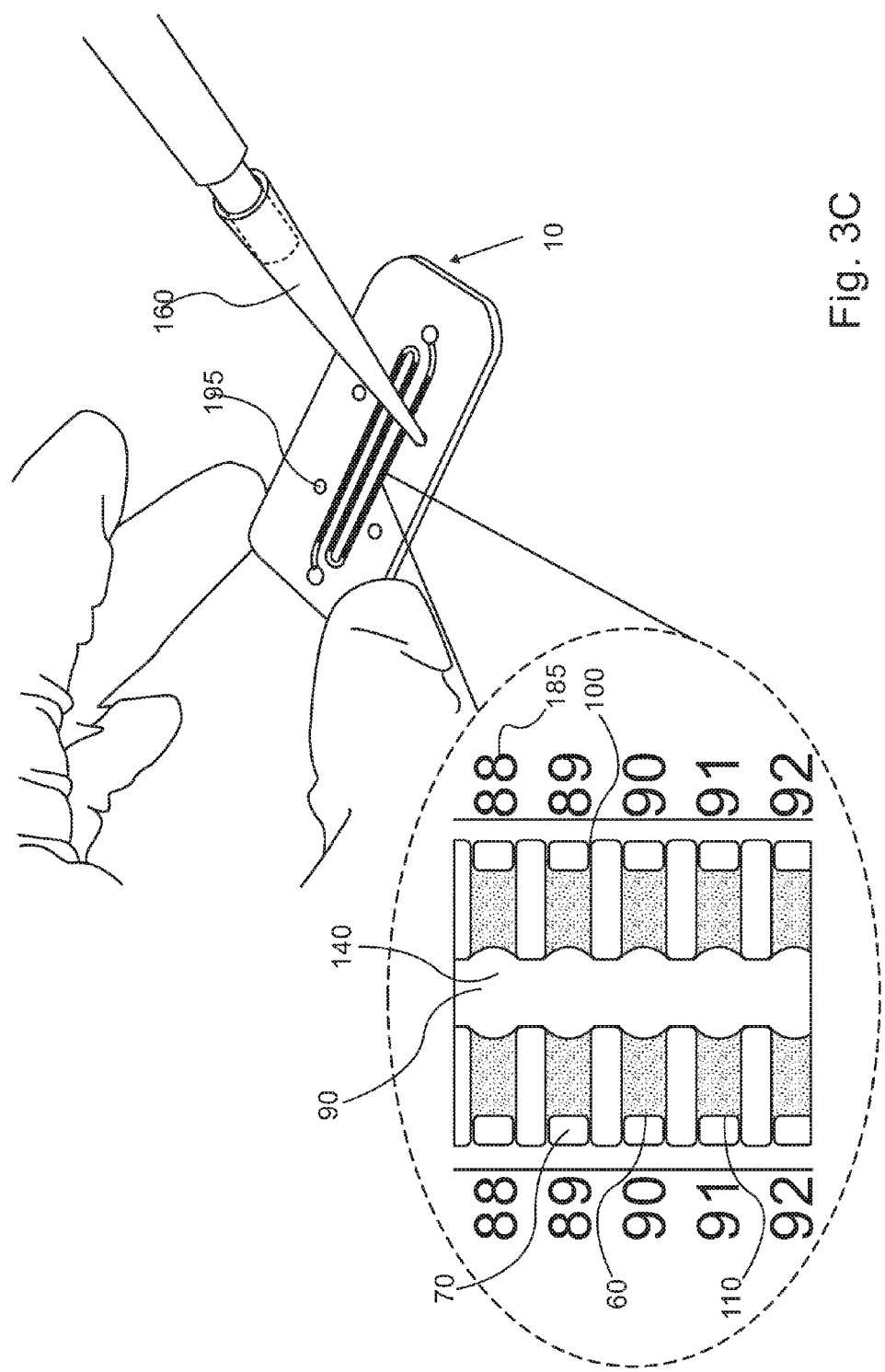

MICROFLUIDIC DEVICE AND METHOD THEREOF

CROSS-REFERENCE TO RELATED APPLICATIONS

This application is a National Phase Application of PCT International Application No. PCT/IL2014/050041, International Filing Date Jan. 15, 2014, claiming the benefit of U.S. Provisional Patent Applications Nos. 61/753,441, filed Jan. 17, 2013, and 61/826,734, filed May 23, 2013, all of which are incorporated herein by reference.

FIELD OF THE INVENTION

The present invention relates to a microfluidic device and methods thereof.

BACKGROUND OF THE INVENTION

There is an increasing interest to investigating single cells, especially over substantial time periods (e.g., days). Microfluidics allows for numerous and creative solutions. In some embodiments, small populations or even single cells are organized into grids, or other organized geometries, where time lapse microscopy and other analyses may be used to monitor and analyze these cells (e.g. monitor their number, morphology or fluorescence variation over time.) In some microfluidic experiments, cells are separated physically or chemically.

Microfluidic devices separate and or interact with cells, other biomolecules, samples, or reagents both spatially and via chemical reactions. Microfluidic devices may offer further insights into the cellular machinery, without the limitation of biochemical cross-talking.

Microfluidic devices are designed to precisely control and manipulate fluids in a geometrically constrained platform. Channels in some devices are microns wide or narrower. Liquids in these channels may be measured in nanoliters or picoliters, i.e., the scale of some typical laboratory science experiments or in inkjet printers.

In some known microfluidic devices the geometric constraints promote environments distinct from those in non-microfluidic devices. The microfluidic environment may differ from the non-microfluidic environment in such ways as laminar flow, surface tension, energy dissipation, diffusion, and fluidic resistance. In a microfluidic environment the flow rate of fluids may be inversely proportional to the square of the area of the channel cross section. In a microfluidic environment fluids may not mix, even when situated side-by-side to one another.

Some known microfluidic devices use capillary action to control or manipulate fluids. Other devices use micropumps or microvalves. Microfluidic devices provide for numerous applications, including for use in biological reactions and the analysis of biomaterials.

Microfluidic devices may be constructed using a variety of manufacturing methods, one such method being, for example, soft lithography. A soft lithography process generally refers to the construction of devices, wherein the construction may employ some techniques similar to standard lithography, i.e., the use of light to transfer structure detailed in a mask onto a silicon wafer. Soft lithography typically employs an elastomer, e.g., a polymer with viscoelasticity, most notably polydimethylsiloxane (PDMS). Soft lithography is generally used to construct features from a wafer die containing a desired pattern, e.g., a pattern that may be appropriate in a microfluidic device, or a stamp for creating such a pattern.

Microfluidics may enable portable analysis devices with short sample-processing times. Microfluidics may provide lab-on-a-chip point-of-care functionality. For example, medical analyses may be able to be conducted at or near the site of the patient care. Other functionality may include immuno-assays, nucleic acid based molecular diagnostics, including application of reverse transcription polymerase chain reaction (RT-PCR) or florescence in-situ hybridization (FISH).

SUMMARY OF THE INVENTION

There is thus provided, in accordance with some embodiments of the present invention, a microfluidic device including a platform with a microstructure including a primary channel and a plurality of chambers that open to the primary channel to enable a sample fluid that is loaded into the device via the primary channel to flow into the plurality of chambers, each chamber of the plurality of chambers having a volume that is less than tens of nanoliters and being connected by a vent to a secondary channel of the microstructure, a width of the vent being configured to enable a gas to escape from the chamber to the secondary channel while inhibiting flow of the sample fluid from the chamber into the secondary channel.

Furthermore, in accordance with some embodiments of the present invention, each chamber of the plurality of chambers is connected to the secondary channel by one or a plurality of additional vents.

Furthermore, in accordance with some embodiments of the present invention, the platform is formed such that one face of the microstructure is covered by a cover that includes an opening to enable fluid flow into or out of the primary channel or the secondary channel via the cover.

Furthermore, in accordance with some embodiments of the present invention, the platform is formed such that one face of the microstructure is exposed allowing attachment of a substrate to cover the exposed face of the microstructure.

Furthermore, in accordance with some embodiments of the present invention, the substrate is removable after attachment to the microstructure.

Furthermore, in accordance with some embodiments of the present invention, the substrate includes glass, plastic, or an elastomer.

Furthermore, in accordance with some embodiments of the present invention, the plurality of chambers includes between 100 and 1000 chambers.

Furthermore, in accordance with some embodiments of the present invention, each chamber of the plurality of chambers is configured to retain a droplet of the sample fluid within that chamber when the sample fluid is removed from the primary channel.

Furthermore, in accordance with some embodiments of the present invention, the chambers are configured to be sealable by introduction of a fluid sealant.

Furthermore, in accordance with some embodiments of the present invention, each of the plurality of chambers is labeled.

There is further provided, in accordance with some embodiments of the present invention, a method for storing droplets of a sample fluid, the method including: introducing the sample fluid via a primary channel of a microstructure into a plurality of chambers of the microstructure that are open to the primary channel, each chamber of the plurality of chambers having a volume that is less than tens of nanoliters and being connected by a vent to a secondary channel of the microstructure, concurrently forcing a gas out of each chamber of the plurality of chambers via the vent into the secondary channel, the vent inhibiting flow of the sample fluid into the secondary channel; introducing a shearing fluid into the primary channel to remove the sample fluid from the primary channel while a droplet of the sample fluid is retained within each chamber of the plurality of chambers; and introducing a fluid sealant into the primary channel and into the secondary channel to isolate the droplet in one chamber of the plurality of chambers from a droplet in another chamber of the plurality of chambers and from an ambient environment.

Furthermore, in accordance with some embodiments of the present invention, introducing the sample fluid, the shearing fluid, or the fluid sealant includes introducing the sample fluid, the shearing fluid, or the fluid sealant via an opening in a cover that covers a face of the microstructure.

Furthermore, in accordance with some embodiments of the present invention, the gas or the evacuated sample fluid is removed from the microstructure via an opening in a cover that covers a face of the microstructure.

Furthermore, in accordance with some embodiments of the present invention, the method further includes attaching a substrate to an exposed face of the microstructure so as to cover that side of the microstructure.

Furthermore, in accordance with some embodiments of the present invention, the method further include removing the attached substrate to enable access to contents of the microstructure.

Furthermore, in accordance with some embodiments of the present invention, the access includes analysis of the droplet in a chamber of the plurality of chambers or removal of the contents from the microstructure.

Furthermore, in accordance with some embodiments of the present invention, the fluid sealant includes a hydrophobic fluid.

Furthermore, in accordance with some embodiments of the present invention, the hydrophobic fluid includes a fluorocarbon oil.

Furthermore, in accordance with some embodiments of the present invention, introducing the sample fluid includes introducing two different sample fluids via different ends of the primary channel to generate a chemically concentration gradient within the primary channel.

Furthermore, in accordance with some embodiments of the present invention, the droplet retained in one chamber of the plurality of chambers is characterized by a chemical concentration that is different from the chemical concentration that characterizes a droplet retained in another chamber of the plurality of chambers.

BRIEF DESCRIPTION OF THE DRAWINGS

In order to better understand the present invention, and appreciate its practical applications, the following Figures are provided and referenced hereafter. It should be noted that the Figures are given as embodiments only and in no way limit the scope of the invention. Like components are denoted by like reference numerals.

FIG. 2A is a schematic illustration of structures on a microfluidic device as the microfluidic device is loaded with samples and reagents, according to an embodiment of the invention;

FIG. 2B depicts a schematic illustration of a step in the loading of a microfluidic device, according to an embodiment of the invention;

FIG. 2C depicts a schematic illustration of a step in the loading of a microfluidic device, according to an embodiment of the invention;

FIG. 2D is a schematic illustration of a step in the loading of a microfluidic device, according to an embodiment of the invention;

FIG. 2E is a schematic illustration of a step in the loading of a microfluidic device, according to an embodiment of the invention;

FIG. 3A is a schematic illustration of the use of a pipette to load a microfluidic device according to an embodiment of the invention;

FIG. 3C is a schematic illustration of the use of a pipette to introduce a fluid sealant into a microfluidic device, according to an embodiment of the invention;

Figure 1:
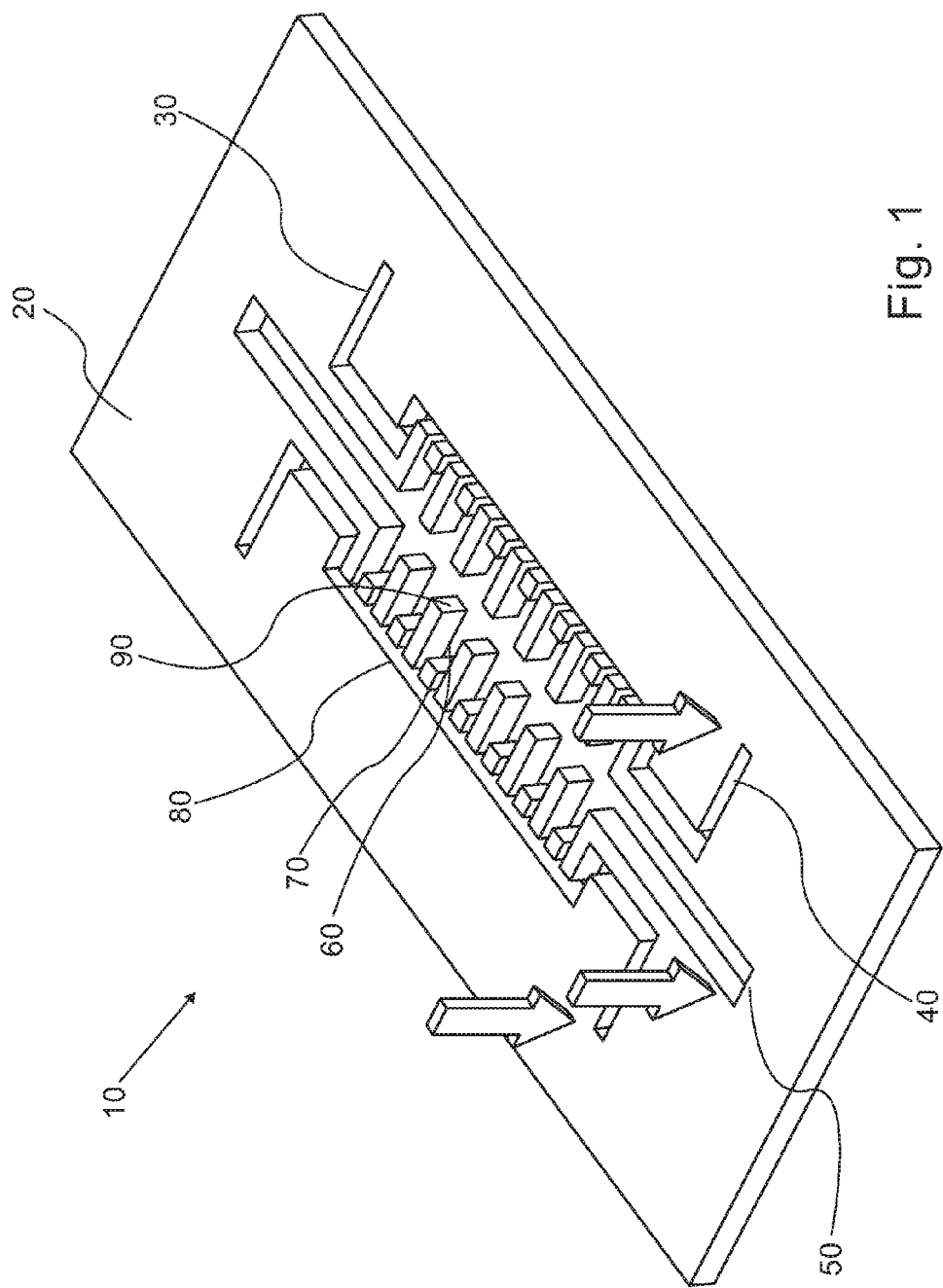
FIG. 1 is a schematic illustration of a representative portion of a microfluidic device according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the embodiments disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed at the same point in time. Unless indicated otherwise, use of the conjunction "or" is inclusive (and should be understood as having the meaning of "and/or").

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions or processes of a computer, computer processor or computing system, or similar electronic computing device, that manipulate, execute or transform data represented as physical, such as electronic, quantities within the computing system's registers or memories into other data similarly represented as physical quantities within the computing system's memories, registers or other such information storage, transmission or display devices.

In accordance with embodiments of the present invention, a microfluidic device is configured to enable introduction of a fluid (e.g., an analyte or another liquid) from an external source into an array of cavities, wells, or chambers. The device enables isolation and sealing of the fluid in each of the chambers. Fluid that is isolated in a chamber is herein referred to as a droplet of the fluid.

In order to simplify the discussion, the introduced fluid may be referred to herein as an "analyte" or as a sample fluid. References to an analyte herein should be understood, unless otherwise indicated, as being interchangeable with references to a sample fluid. As used herein, an array of chambers should be understood as referring to any regular, semi-regular, or irregular pattern of chambers. For example, a sample fluid (typically a liquid) may include water, polysorbate 20 (Tween 20®), or normal human dermal fibroblast (NHDF) cell medium, or another fluid. As used herein and unless specified otherwise, the term "fluid" may refer to a liquid or a gas. For example, in some embodiments described herein, sample fluids and fluid sealants (described below) are primarily liquids, and shearing fluids (described below) are primarily gasses. However, other types of fluids may be used, or the fluid may change state during or after usage.

The microfluidic device includes a platform with a microstructure of channels, chambers, and separating walls. For example, the microstructure may be formed together with the platform, e.g., in a molding, spin coating, or stamping process, or may be formed in an existing platform, e.g., using an etching, micromachining, or photolithography process. Typically, the platform is a flat structure with two large, substantially parallel faces (e.g., rectangular, or having another shape) connected by edges (typically, substantially parallel to the faces) whose small dimension is much smaller than any dimension of either of the faces. The microstructure is arranged substantially parallel to the faces, such that any cross section through the microstructure that is parallel to the faces is substantially identical to any other. (The platform may have another shape, e.g., non-flat shape with a curved or bent face, e.g., in the form of a spherical, spheroid, polyhedrical, or otherwise-shaped thin shell.)

Typically, one face of the platform includes a cover that prevents access to the microstructure via that face except via a limited number of openings in the cover. Typically, the opposite face of the microstructure is exposed. The exposed face may be covered prior to, or during, use of the microfluidic device by attachment of a substrate.

The microstructure includes a pattern of elongated channels that is provided to connect the chambers to one or a plurality of openings to the outside of the device. Small quantities (e.g., nanoliter-sized droplets) of the sample fluid may be stored isolated from one another within the chambers. The chambers may be rectangular or square, or may have any other shape having flat or curved walls (e.g., polygonal, round, oval, or other shape).

As used herein, a device is described as microfluidic, or a structure of a device is described as a microstructure, when the dimensions of various components (e.g., chambers or channels) of the device satisfy various conditions. Such conditions may include, for example, that a volume of a chamber not exceed 100 nanoliters (nl), that a longest dimension of a chamber not exceed 1 mm, or that a small dimension (e.g., width or height of an elongated structure) not exceed 500 µm.

The chambers may be herein referred to as nano-wells when the volume of each chamber is less than tens of nanoliters. (As used herein, the term "tens of nanoliters" should be understood as referring to less than 100 nl.) In some cases, the volume of each chamber may be less than 10 nl. In some cases, the volume of each chamber may be less than 1 nl (e.g., 0.3 nl). The chambers and channels are herein collectively referred to as a microstructure.

The microstructure is typically arranged in a substantially flat pattern. For example, the chambers and channels may be formed by using one or more techniques (e.g., micromachining techniques, molding, photolithography, or other techniques) to remove material from a flat platform to form the chambers and channels. A cover that includes openings to the outside may be permanently attached to the platform that includes the microstructure. In other embodiments, the platform, microstructure, and cover may be formed in a single process (e.g., microlithography). A combination of different formation processes may be used. When placed horizontally for use, the microfluidic device is placed such that the cover with the openings to the outside faces upward.

The other (e.g., opposite the cover) side of the microstructure may be closed or sealed by attachment of a substrate. For example, the substrate may be made of, or include, glass (e.g., a glass slide), plastic or polymer (e.g., a tissue culture plate), an elastomer, or other material suitable for closing a side of the microstructure. The substrate may be selected for a particular application. For this purpose, a substrate of a particular material may be selected, or the substrate may be coated or silanized with a material (e.g., patterned proteins) in order to achieve a desired property. For example, the substrate may be selected to enable particular characteristics of flow of a particular fluid within the microstructure (e.g., hydrophobicity or hydrophilicity). The substrate may be selected or coated to affect behavior of cells that are included in the sample fluid. For example, substrate may be coated selected to induce cell attachment, to affect cell growth in a particular manner, or to facilitate analysis of cells. The attachment of the substrate to the microstructure may be such as to enable later removal of the substrate, e.g., to enable access to, or disposal of, the sample fluid in the chambers or fluid in the channels. When the microfluidic device is in use, the side sealed by the substrate is typically at the bottom of the microfluidic device. For example, in this manner, a sample fluid is kept in contact with the substrate by gravity.

Each chamber includes an opening that connects the chamber to a primary channel. A sample fluid may be introduced into each chamber via the primary channel (and via an opening in the cover or elsewhere through which the sample fluid may be introduced into the microstructure from outside the microfluidic device). For example, a sample fluid may be injected into an opening in the cover that connects either directly or indirectly (e.g., via an intervening channel) to the primary channel.

Prior to introduction of the sample fluid into the chamber, the chamber may have previously been filled by a gas (e.g., air) or by another fluid that is significantly less viscous than the sample fluid. For example, the microfluidic device, prior to filling with sample fluid, may have kept in a controlled atmosphere or environment from which air was excluded. For simplicity, the fluid previously filling the chamber is herein referred to as air. References herein to air that fills the chamber prior to introduction of the sample fluid should be understood, however, as referring to air or any other gas (or extremely low viscosity liquid) that fills the chamber prior to introduction of the sample fluid. Each chamber is connected to a secondary channel, herein referred to also as an evacuation channel, via a vent structure. The evacuation channel is connected, either directly or indirectly (e.g., via an intervening channel), to an opening in the cover (or elsewhere) that opens to the ambient environment.

The vent structure is typically located on a side of the chamber opposite to the opening to the primary channel, or on any other side of chamber (such that the vent does not open to the primary channel). The structure includes an arrangement of one or a plurality of narrow slits that connect the interior of the chamber to the evacuation channel. The structure of each slit is such that the air may readily flow from the chamber into the evacuation channel through the slit. The slit is sufficiently narrow, however, to inhibit or prevent the sample fluid from exiting the chamber through the slit without application of a pressure that is appreciably greater than the pressure that is applied to introduce the sample fluid. In the absence of such greater pressure, various forces (e.g., one or more of surface tension or Laplace pressure, adhesive forces, and ambient pressure) resist motion of the sample fluid outward through the slit to the evacuation channel. Each such slit is hereinafter referred to as a vent. Thus, the vent structure includes a single vent, and may include one or a plurality of additional vents.

As used herein, a vent is considered to inhibit flow of a fluid when, at a given pressure with which the fluid is introduced into the microstructure, flow of the fluid through the vent is prevented. The pressure may, in some cases, be close to (e.g., no more than 101% of) atmospheric pressure. In other cases, e.g., when using a pipette to introduce a fluid, the pressure may significantly exceed atmospheric pressure.

A microfluidic device in accordance with embodiments of the present invention, each whose chambers includes a vent and an evacuation channel, may be advantageous over a device with a different structure. The vent may enable the air (typically at atmospheric pressure, or another gas at a pressure that is close to atmospheric pressure) to be readily evacuated from the chamber through the vent as a result of introduction of the sample fluid. In a device without such a vent and without application of high pressure, bubbles of a fluid previously filling the chamber (e.g., air) could prevent complete filling of the chamber by the sample fluid.

Thus, a sample fluid may be introduced into chambers of a microfluidic device in accordance with embodiments of the present invention at a relatively low pressure (e.g., that does not need to overcome the resistance of air bubbles to force fluid into the chambers). Since the attachment of the substrate to the remainder of the device need not withstand high pressure, a reversible mechanism may be used to non-permanently attach the substrate to the remainder of the device. For example, an elastomeric substrate with a tacky surface may self-adhere to the microstructure. Alternatively or in addition, the substrate may be held in place by gravity in combination with ambient atmospheric pressure, or a weak adhesive may be used. Since low pressure is involved, a strong or permanent bond is not required to prevent leakage out of the microfluidic device. As a result, the substrate may be removable, enabling access to the contents of the chambers. Removing the substrate may also expedite removal or some or all contents of the chambers at a later time. Removing the contents may enable further analysis of the contents outside of the microfluidic device, or cleaning and reuse of the microfluidic device.

After introduction of the sample fluid into the chambers via the primary channel, the sample fluid in the primary channel may be removed. The operation of removing a fluid from the primary channel while retaining fluid in the chambers is herein referred to as shearing. For example, air or another shearing fluid (typically a gas) may be introduced into the primary channel via an opening in the cover that is functioning as an inlet. The shearing fluid may force the sample fluid out of the primary channel via another opening that is functioning as an outlet. The removed or sheared sample fluid may be absorbed by an absorbent material upon exit via the outlet. The chambers are configured (e.g., by being characterized by various design characteristics, e.g., relating to shape or surface properties) to retain the sample fluid within the chambers during shearing.

After introduction of the sample fluid into the chambers, the chambers may be sealed off by introduction of a fluid sealant. Sealing off the chambers may enable retention of the introduced field by preventing evaporation or leakage. Sealing off the chambers may also serve to isolate the sample fluid in each chamber from sample fluid in the other chambers. Sealing off may be performed after shearing (or may be performed concurrently with shearing, e.g., if a fluid sealant is used as the shearing fluid).

For example, a fluid sealant that does not chemically react with the sample fluid may be introduced via openings (e.g., in the cover) into the various channels of the microfluidic device. A suitable fluid sealant may include, for example, a fluorocarbon oil. Introduction of the fluid sealant into a primary channel isolates the filled chambers from one another and from the ambient environment. Introduction of the fluid sealant into an evacuation channel removes air from the evacuation channel, further isolating the sample fluid in the filled chamber from contact with the ambient environment via the vents. After introduction of the fluid sealant, isolated samples of the sample fluid may be kept in isolation from one another and from the ambient environment until removal of the substrate from the remainder of the device. After sealing, or at any other point, the opening (e.g., in the cover) may be sealed to prevent evaporation or otherwise isolate contents of the microfluidic device from the environment.

Each chamber may be marked (e.g., on an adjacent section of the cover) in a manner that provides a unique identification of each chamber. The marking may be identifiable by viewing through a microscope or otherwise.

Removable attachment of a substrate to the microfluidic device may be advantageous. The substrate may be removed and replaced at different times to enable contact with various samples held in various chambers of the microfluidic device. A substrate may be selected that is suitable to a particular application. For example, different substrates may have different affinities to different sample fluids or components of sample fluids. Different substrates may enable different mobility of a sample fluid or sample fluid component within the microfluidic device. Thus, selection of a particular substrate may be advantageous in performing long-term single cell analysis on adherent cells. A microfluidic device with removable attachment of a substrate may be advantageous in performing proliferation and metabolism tracking in mammalian cells or tissue, bacteria, or other cells. Cell secretion can be monitored in the chemically isolated wells. Coated substrates (e.g., with antibodies or other molecules used in detection) may be utilized in detection or analysis of adherent promoting or non-promoting patterns.

According to some embodiments of the invention, droplets of a sample fluid (e.g., in the manner described hereinafter) may be designed to contain an unknown, known, or variable concentration of the sample fluid. Sample fluids contained in a droplet may include, for example, cells, proteins, small molecules, metabolites, nucleic acids, molecules, biomolecules, or other assayable substances. A droplet may remain stable and stationary, in some embodiments of the invention, due to geometrical or other constraints. For example, geometrical constraints may include a rectangular shape of a chamber of the microfluidic device. Other constraints may result from a material from which a surface of the device is constructed. In some embodiments, there may be no detectable evaporation of a droplet over an extended period of time.

The flow of a sample fluid through a microfluidic device may be characterized by the Reynolds number of the device. The Reynolds number is a dimensionless quantity that is equivalent to the ratio of inertial forces to viscous forces within an arrangement of a fluid that is flowing around or between surfaces. The Reynolds number is indicative of the type of fluid flow (e.g., laminar or turbulent) in the arrangement.

The Reynolds number (Re) may be expressed as:

$$Re = \frac{\rho v L}{\mu}$$

where v is the mean velocity of the object relative to the fluid (e.g., in meters/second); L is a characteristic linear dimension, e.g., length (e.g., in meters); μ is the dynamic viscosity of the fluid (e.g., in kilograms/(m·s)); and ρ is the density of the fluid (e.g., in kg/m$^3$).

In some embodiments of the present invention, the Reynolds number for flow of the sample fluid within the microfluidic device may be less than 100, and in some microfluidic devices, the Reynolds number may approach or be less than 1. When the Reynolds number is 100 or less, flow through the microfluidic device is completely or nearly completely laminar, and no turbulence occurs in the flow. When flow is laminar, molecules can be transported through channels in the microfluidic device in a relatively predictable manner.

In some embodiments, the microfluidic device may be applied to enable viewing, measurement, or analysis with regard to various biochemical or molecular scenarios. Such scenarios may include, for example, cell-to-cell signaling and interactions, time-versus-exposure measurement of a cellular response of an individual cell to chemical stimulation, dose-response relationships, screening of bacterial strain resistance to antibiotic drugs, prokaryotic-single-cell investigation in highly isolated environments, and cellular uptake and excretion.

A microfluidic device may also be used to enable or expedite conduction, viewing, measurement, or analysis of rapid tests of antibiotic susceptibility against different pathogen species, single cell secretion assays monitored over long incubation periods, single molecule polymerase chain reaction (PCR) dilutions (e.g., such that each droplet contains a single deoxyribonucleic acid (DNA) molecule), RT-PCR performed on a single cell, immunoassays, or application of other biological or non-biological methodologies.

In some embodiments, the microfluidic device may be recyclable or may enable reversible attachment of a substrate to the microfluidic device. Use of a microfluidic device may be advantageous as providing for simplicity of use, cell retrieval, or surface patterning. The microfluidic device may be used to isolate or store use small amounts of sample fluid, e.g., on a microliter, nanoliter, or picoliter scale. The sample fluid may include, for example, analytes, body fluids, hydrophobic fluids, or other reagents. The microfluidic device may be configured for the loading of a fluorocarbon oil or other fluid sealant.

The microfluidic device may not require use of a fluorocarbon-based surfactant in the loading process. The microfluidic device may allow for soft-lithography fabrication, without a plasma oxygen sealing step. The microfluidic device may allow for easy setup and loading.

FIG. 1 is a schematic illustration of a representative portion of microfluidic device 10, according to an embodiment of the invention.

In some embodiments, a microfluidic device may be configured to include repeating monomers of the representative portion of a microstructural pattern described, for example, herein. In some embodiments a microfluidic device may be configured to include the representative portion shown herein or a combination of similar and different portions as components of a microfluidic device. In some embodiments a microfluidic device may be compartmentalized to include the representative portion shown herein and other portions unrelated to, or distinct from, the representative portion. In some embodiments a microfluidic device may be configured such that some portions of the device are designed to contain different volumes in their respective chambers, e.g. the chambers as described below. In some embodiments a microfluidic device may be configured such that portions of the microfluidic device containing different volumes in their respective chambers may be used to compare the behavior of analytes, molecules, cells or other samples in different volumes.

In FIG. 1, microfluidic device 10 is shown without cover 22 (visible in FIG. 6B), in order to enable viewing of internal structure. Typically, cover 22 is permanently bonded to, or is integral to (e.g., formed of a continuous piece of material with) platform 20. In some embodiments, cover 22 is transparent to enable viewing the interior of microfluidic device 10. Cover 22 may contain one or more ports or openings to enable fluids (e.g., air, sample fluid, or fluid sealant) to be introduced into or removed from the interior of microfluidic device 10.

Microfluidic device 10 includes a platform 20. Platform 20 may be made from various materials. For example, platform 20 may be made from a polymer, such as, for example, polydimethylsiloxane (PDMS or dimethicone), or another suitable polymer or material. Platform 20 may include one or a plurality of microstructures 30. Microstructures 30 may include various indentations or hollowed out microstructural patterns comprising a primary channel 90, one or a plurality of secondary channels 80, chambers 60 branching off primary channel 90, and vents 100 (shown in FIG. 2) separated by separating walls. Microstructures 30 may rest directly or indirectly on platform 20. Platform 20 may be constructed of or include the same material or a similar material to that of microstructures 30. Platform 20 may be constructed of a distinct material from microstructures 30, for example, microstructures 30 are prefabricated and attached to a separate platform 20. In some embodiments microstructures 30 may be manufactured using a process that is associated with soft lithography. The process may include the construction of a master, e.g., in the form of a master plate or mold, using, for example, photolithography, e-beam, micro-machining, or another technique. An elastomer, such as PDMS, may be poured, spin casted, or otherwise applied to a master plate or into a mold and cured (e.g., by application of heat or ultraviolet light) or hardened. Once cured or hardened, the elastomer may be peeled away or otherwise removed from the master or mold, resulting in a set of micro-structural patterns that are the inverse of those on the master. The peeled away PDMS mold may be used as a microfluidic device, or it may be used as stamp to transfer the patterns and structures of the master to another surface or platform.

In some embodiments on the invention, microfluidic device 10 may be manufactured using a deep reactive-ion etching (DRIE) technique. DRIE is an anisotropic etching process that may be used to create deep penetration, steep-sided holes or trenches in substrates. DRIE may be cryogenic (i.e., wherein the substrate is pre-chilled prior to the chemical etching), or may use a Bosch process (pulsed or time-multiplexed etching). DRIE may enable achievement of higher resolutions that with other processes, which may enable microfluidic device 10 to operate over a wide range of pressures.

Microstructures 30 may be manufactured using other or additional processes. Microstructures 30 may be single tiered or multi-tiered. The microstructural patterns may be configured to provide functionality for microfluidic device 10. Different microstructural patterns may be employed with one or a plurality of microfluidic devices 10, depending on the nature of the sample, reagent or other fluids (e.g., sample fluid or fluid sealant) intended to be used with microfluidic device 10. Different microstructural patterns may be used with microfluidic device 10, e.g., depending on the external environment of microfluidic device 10 or other criteria.

Microstructures 30 may include channels, pumps, valves, chambers, chambers, vents or other components in a microfluidic device.

Microfluidic device 10 has a plurality of secondary inlets 40 and one or a plurality of primary inlets 50. In some embodiments, microfluidic device may include additional access ports or inlets, including one or a plurality of side or secondary inlets 40 and one or a plurality of primary inlets 50. For example, each primary channel 90 may be provided with two primary inlets 50. In use, one of the primary inlets 50 may function as an inlet during introduction of a sample fluid into microfluidic device 10, and the other as an outlet for the sample fluid during introduction of a fluid sealant. Similarly, each secondary channel 80 may be provided with two secondary inlets 40. Typically, primary inlets 50 and secondary inlets 40 are located near the ends of their corresponding primary channel 90 and secondary channel 80, respectively.

Each primary inlet 50 or secondary inlet 40 is accessible from outside of microfluidic device 10 via a port or opening in cover 22. For example, each opening is placed above its corresponding primary inlet 50 or secondary inlet 40. In some embodiments, inlets may be shaped to resemble circles. In other embodiments, inlets may have other geometries. In some embodiments, inlets may be configured to enable introduction or escape of sample fluids, analytes, fluid sealants, reagents, propellants or other fluids. Propellants may be configured to move samples, reagents, or other fluids through microfluidic device 10. Propellants may include air. Inlets or their corresponding openings may be a component of the master, as described, for example herein, or may be added after the mold has been copied from the master.

Microfluidic device 10 includes compartments, hollows, chambers, wells, nano-wells, or cavities, represented by chambers 60. Chambers 60 are included in microstructures 30 in microfluidic device 10. Chambers 60 may be configured to accept or contain inert, biological, organic, inorganic, or other types of sample fluids or analytes. Chambers 60 may be configured to accept or contain reagents or other fluids. A geometric shape of each chamber 60 may be in the form of, or similar to a square, rectangle, circle, or other shape. Chambers 60 may be characterized by a defined area and a volume. Some or all of chambers 60 may be open to an external or outside environment, or may be sealed from an external or ambient environment.

In some embodiments of the invention, an open side of microfluidic device 10 (e.g., a side lacking cover 22) may sealed by attachment of a substrate 15. For example, substrate 15 may be attached prior to use. Substrate 15 may be reversibly or irreversibly (permanently) attached. Attachment may include application of oxygen plasma treatment, which may serve to remove organic surface contamination via a chemical reaction with the surface contaminants.

Microfluidic device, portions thereof, or chambers 60 may be sealed from the external environment via a substrate 15. Substrate 15 may include glass, polylysine, poly-L-lysine treated glass, a tissue culture dish, a non-tissue-culture dish (polystyrene), PDMS, a Petri dish, a microscope slide, or other suitable component.

Microfluidic device 10 includes side channel 80 and primary channel 90. Microfluidic device 10 may have one or a plurality of additional channels. In some embodiments additional channels may include one or a plurality of side channels 80, primary channels 90, or other channels. Channels may have diameters in the range 10 μm-500 μm. In some embodiments of the invention, channels may have wider diameters. In some embodiments of the invention, channels may have narrower diameters. Volumes of the channels may be in the range of nanoliters (e.g., from less than 1 nl, e.g., 0.3 nl or less, to tens of nanoliters, e.g., 8 nl or more). Channels may be configured to allow sample fluids, reagents, propellants, analytes, processed samples, processed reagents, processes propellants, or other fluids to enter chambers 60. Processing of analytes, sample fluids, reagents, propellants, or other fluids may include shearing.

Microfluidic device 10 may have one or a plurality of exit ports. The exit ports, for example as described below, may be configured to allow a user to extract sample fluids, reagents, propellants or other fluids from microfluidic device 10, including samples, impurities, or propellants evacuated from primary channel 90.

Microfluidic device 10 may have additional access ports or inlets to allow the introduction of samples, reagents, propellants other fluids or fluorocarbon based oils into microfluidic device 10.

A chambers 60 may be separated from other structure by one or more walls 70. Some or all of walls 70 may include vents, as described, for example, herein with reference to FIG. 2A-2E. In some embodiments of the invention, a chamber 60 may be configured to have walls 70 defining an area, a volume or partially defining an area or volume. In some embodiments, there may be one or a plurality of walls 70 defining the area or volume of a chamber 60. In some embodiments, walls 70 may be continuous. Walls 70 of chambers 60 may be discrete or non-contiguous. Discrete or non-contiguous walls 70 may have neighboring walls. Walls 70 may or may not have gaps between neighboring walls.

In accordance with some embodiments of the present invention, chambers 60 may have volumes measurable in picoliters or nanoliters. Individual structures of microstructures 30 may have dimensions measurable in micrometers up to millimeters.

In accordance with some embodiments of the present invention, microfluidic device 10, or a subset of microstructures 30 on microfluidic device 10, may be characterized by an area of 60 millimeters (mm)×24 mm. Microfluidic device 10 may be configured to provide area and volume for 600 droplets of a sheared sample per device. In some embodiments, microfluidic device 10 may be configured to provide area and volume for a greater or smaller amount of droplets of a sample.

In accordance with some embodiments of the present invention, microfluidic device 10 may be configured such that each droplet of a sheared sample may have a volume defined by the dimensions 400 µm×200 µm×100 µm. Each droplet may have a volume defined by dimensions that are in some embodiments greater, or in some embodiments, less than these dimensions. Microfluidic device 10 may be configured such that each sample droplet has a volume of 8 nanoliters. Microfluidic device 10 may be configured such that each sample droplet has a greater or lesser volume than 8 nanoliters.

In accordance with some embodiments of the present invention, microfluidic device 10 may be configured such that the total volume of sample fluid used is 15 µl and the total volume of a fluid sealant used is 40 µl. A Microfluidic device 10 may be configured such that the total volume of sample fluid is greater than or less than 15 µl, and the total volume of fluid sealant used is greater than or less than 40 µl.

Microfluidic device 10 may be configured such that no surfactants are used in loading, unloading, or in analysis of a sample fluid. Microfluidic device 10 may be configured such that surfactants may be used in loading, unloading, or in analysis of a sample fluid. Microfluidic device 10 may be configured such that loading time may be approximately 5 minutes. Microfluidic device 10 may be configured such that loading time may be more or less than 5 minutes.

Microfluidic device 10 may be loaded manually, semi-automatically, or automatically. Microfluidic device 10 may be loaded using a pipette, a pipette bulb, vacuum aspiration, or other device or technique.

In some embodiments, microfluidic device 10, or a subset of microstructures 30 on microfluidic device, may have an area of 60 millimeters (mm)×24 mm. Microfluidic device 10 may be configured to provide area and volume for 200 sheared sample droplets per device. In some embodiments, microfluidic device 10 may be configured to provide area and volume for a greater or smaller amount of sample droplets.

Microfluidic device 10 may be configured such that each sample droplet may have a volume defined by the dimensions 80 µm×80 µm×50 µm. Each sample droplet may have a volume defined by dimensions that are in some embodiments greater than, or in some embodiments less than, these dimensions. Microfluidic device 10 may be configured such that each sample droplet has a volume of 0.3 nanoliters.

In accordance with some embodiments of the present invention, microfluidic device 10 may be configured such that each sample droplet has a greater or smaller volume than 0.3 nanoliters. Microfluidic device 10 may be configured such that the total volume of sample fluid used is 15 µl, and the total volume of fluid sealant used is 40 µl. Microfluidic device 10 may be configured such that the total volume of sample fluid used is greater or less than 15 µl, and the total volume of fluid sealant used is greater or less than 40 µl.

Microfluidic device 10 may be configured to provide area and volume for different numbers of sheared sample droplets per device. Microfluidic device 10 may be configured to provide area and volume for less than 200 sheared sample droplets per device, e.g., 100. Microfluidic device 10 may be configured to provide area and volume for more than 600 sheared sample droplets per device, e.g., less than 1000 chambers.

In some embodiments of the invention, microfluidic device 10 may be configured to provide area and volume for between 100 and 200 droplets per device, e.g., within 100 to 200 chambers 60. In some embodiments of the invention, microfluidic device 10 may be configured to provide area and volume for between 200 and 300 droplets per device, e.g., within 200 to 300 chambers. In some embodiments of the invention, microfluidic device 10 may be configured to provide area and volume for between 300 and 400 droplets per device, e.g., within 300 to 400 chambers. In some embodiments of the invention, microfluidic device 10 may be configured to provide area and volume for between 400 and 500 droplets per device, e.g., within 400 to 500 chambers. In some embodiments of the invention, microfluidic device 10 may be configured to provide area and volume for between 500 and 600 droplets per device, e.g., within 500 to 600 chambers. In some embodiments of the invention, microfluidic device 10 may be configured to provide area and volume for between 600 and 700 droplets per device, e.g., within 600 to 700 chambers. In some embodiments of the invention, microfluidic device 10 may be configured to provide area and volume for between 700 and 800 droplets per device, e.g., within 700 to 800 chambers. In some embodiments of the invention, microfluidic device 10 may be configured to provide area and volume for between 800 and 900 droplets per device, e.g., within 800 to 900 chambers. In some embodiments of the invention, microfluidic device 10 may be configured to provide area and volume for between 900 and 1000 droplets per device, e.g., within 900 to 1000 chambers. In some embodiments of the invention, microfluidic device 10 may be configured to provide area and volume for greater than 1000 droplets per device, e.g., within greater than 1000 chambers. In some embodiments of the invention, microfluidic device 10 may be configured to provide area and volume for less than 100 droplets per device.

In accordance with some embodiments of the present invention, chambers 60 may be arranged opposite one another on both sides of a linear primary channel 90, as shown in FIG. 1. In accordance with some embodiments of the present invention, all or part of chambers 60 may have another configuration. For example, chambers 60 may be arranged such that all are on one side of primary channel 90. Chambers 60 may be arranged such that chambers 60 on one side of primary channel 90 are staggered (e.g., not directly opposite) chambers 60 on the other side. Primary channel 90 may have a curved, bent, spiral, or other form, with chambers 60 being arranged about primary channel 90 accordingly. Other arrangements may be used.

FIG. 2A is a schematic illustration of structures on a microfluidic device as the microfluidic device is loaded with samples and reagents, according to an embodiment of the invention.

FIG. 2A depicts a representative sample of a portion or subset of restrictions or microstructures 30 within microfluidic device 10. Chambers 60 are enclosed by walls 70. Walls 70 include vents 100. In some embodiments, chambers 60 may be defined, enclosed, or partially enclosed by walls 70. Walls 70 may be constructed using soft lithography methods and may be made of PDMS. Walls 70 may be constructed using other methods or from other materials. Some of walls 70 may be contiguous. Some of walls 70 include vents 100. In some embodiments of the invention, each chamber 60 may include two vents 100. In some embodiments of the invention, each chamber 60 may include more than two vents 100.

Vents 100 may be configured to allow for fluidic communication between chambers 60 and one or a plurality of secondary channels 80. Fluid communication may allow for the evacuation of air or another fluid, an impurity or other reagent from chambers 60. Vents 100 may be configured to be sealable or limit the evacuation or the escape of a sample fluid from chamber 60. Vents 100 may be configured such that air may flow through vent 100, but a sample fluid is restricted from passing through vent 100. In some embodiments of the invention, a smaller vent size provides for a wider pressure range, for example, in a shearing step as described, for example, below.

Chambers 60 branch off of primary channel 90. Chambers 60 are configured such that they face other chambers 60 across a primary channel 90. In some embodiments of the invention, chambers 60 may be configured such that they are staggered across primary channel 90. Chambers 60 may be configured such that there are no other chambers 60 across primary channel 90. Chambers 60 may be configured such that there are an equal, greater or smaller number of chambers 60 across primary channel 90.

Primary channel 90 may loop, meander or otherwise curve within microfluidic device 10. In some embodiments of the invention, primary channel 90 may run in a single straight path, line, or direction.

In some embodiments, chambers 60 may be fabricated such that the area of the chamber resembles a rectangle. Chambers 60 may be fabricated such that the area of the chamber resembles another geometric shape.

In some embodiments of the invention, chambers 60 may be fabricated such that side channels 80 are on a side opposite the side of chambers 60 facing primary channel 90. Chambers 60 may be indexed or labeled. In some embodiments of the invention chambers 60 may not be indexed. More than one chamber 60 may share an indexing identification number or designation.

In some embodiments of the invention, side channels 80 may be configured to allow air to exit or be evacuated from one or a plurality of chambers 60 into side channels 80 via vents 100. Side channel 80 may be connected to chambers 60 via one or a plurality of vents 100 in walls 70. Vents 100 may allow air or foreign matter, undesirable matter, or another contaminant to exit from chambers 60 when a sample fluid in the form of sample fluid 110 is introduced into chambers 60. Thus, vents 100 may facilitate the entry of sample fluid into chambers 60. In this manner, side channel 80 functions as an evacuation channel, as described above.

FIG. 2B depicts is a schematic illustration of a step in the loading of a microfluidic device, according to an embodiment of the invention.

FIG. 2B depicts a step in loading microfluidic device 10. Sample fluid 110, for example, an analyte (or another fluid), is introduced into microfluidic device 10 and into primary channel 90. In some embodiments of the invention, sample fluid 110 may be loaded or otherwise introduced into primary channel 90. Sample fluid 110 may be introduced into primary channel 90 via inlets. Sample fluid 110 may be introduced into other channels or via other inlets or ports, e.g., a port or opening in a cover.

Sample fluid 110 is caused to flow through primary channel 90 and into chambers 60 as depicted by arrows 115. In some embodiments of the invention, sample fluid 110 may flow in additional directions. Sample 110, while flowing or otherwise passing through primary channel 90, may also enter a plurality of chambers 60 or other microstructures 30, or a subset of microstructures 30 within microfluidic device 10. Primary channel 90, secondary channels 80, vents 100, or chambers 60 may be filled with air (or another fluid) prior to the introduction of sample 110. Sample fluid 110 may displace the air present in microfluidic device 10, in chambers 60, or other components of microfluidic device 10. The displaced air may exit from chambers 60, or from other connecting microstructures 30, via vents 100.

In some embodiments, microfluidic device 10 may be used to generate an array of sample droplets with variable chemical concentrations. This variable chemical concentration throughout the microfluidic device may be attainable when an additional fluid loading step is done prior to a shearing step, the shearing step described, for example, below.

In some embodiments of the invention, secondary channels 80 may be configured to enable air to escape from the microfluidic device. When adding multiple fluids into the device, the secondary channels may allow the escape of air or other gasses.

In some embodiments of the invention, an inlet of the microfluidic device may have a depth height of, e.g., 1 mm-6 mm, in some examples 4 mm. (For example, the depth of the inlet may be approximately equal to a thickness of the microfluidic device.) The pressure of the fluid in this inlet may cause a flow of liquid from one side of the microfluidic device to another side, in a controlled manner, the controlled manner being dictated by the depth of the inlet and a time delay due to mixing of the fluids.

In some embodiments of the invention, a second or subsequent fluid may be introduced into an inlet, for example, as described above. The second or subsequent fluid may be introduced into an inlet via a pipette or other device. The second and or subsequent fluid may be pushed into microfluidic device 10 using air pressure, or pulled into the device by application of a vacuum to an outlet. Air pressure or vacuum may be created by a pipette bulb or other devices or sources.

In some embodiments of the invention, chambers 60 that are closer in proximity to the inlet may have a higher concentration of the second fluid and or sample fluid 110 compared to chambers further away in proximity to the inlet resulting in an array of droplets in a chemical gradient through the chambers of microfluidic device 10.

The chemical gradient may be reflected in concentrations of components of the fluid that is captured in each of chambers 60 after shearing, as described, for example, below.

In some embodiments of the invention, a gradient may be generated by injecting two different fluids. A first fluid may be injected from a first inlet and a second fluid may be injected into the microfluidic device via an outlet (or second inlet). The first fluid and the second fluid may meet at an interface at a point along primary channel 90, e.g., near a midpoint, where the two fluids meet. The concentration of the first and second fluids may be related to the upper limit and lower limit of the concentrations of the mixed fluids.

Convection forces may mix the first and second fluids at the interface between the first and second fluids. A length of a period of time during which the convection forces mix the first and second fluids may determine the concentration difference between adjacent droplets resulting from a shearing of the fluids.

FIG. 2C depicts a schematic illustration of a step in the loading of a microfluidic device according to an embodiment of the invention.

FIG. 2C depicts a shearing step in loading microfluidic device 10. Sample fluid 110 is sheared by the introduction of a shearing flow, in some embodiments of the invention, via a shearing fluid 120. The direction of shearing fluid 120 is depicted by arrows 130. In some embodiments of the invention, the shearing fluid may be a fluid combined with shearing forces, e.g., air pushed through microfluidic device 10. In some embodiments, air may be introduced or pushed through microfluidic device via a bulb, pipette, or other device. The shearing force of shearing fluid 120 may expel sample fluid 110 out of channels, including primary channel 90. Thus, the shearing force of shearing fluid 120 may separate sample fluid 110 into individual droplets of sample fluid 110 in separate chambers 60. The direction of flow of shearing fluid 120 is depicted by arrows 130. Shearing fluid 120 may flow in additional directions.

FIG. 2D depicts is a schematic illustration of a step in the loading of a microfluidic device according to an embodiment of the invention.

FIG. 2D depicts the loading of fluid sealant 140, e.g., a hydrophobic fluid such as an oil, into microfluidic device 10. Arrows 150 depict the flow of fluid sealant 140 through channels in microfluidic device 10. In some embodiments, additional reagents may be added to microfluidic device 10 prior to this step of loading fluid sealant 140.

In some embodiments of the invention, fluid sealant 140 may include fluorocarbon oil (e.g., 3M™ Fluorinert™ Electronic Liquid FC-40). Fluid sealant 140 may include other reagents. In some embodiments of the invention, fluid sealant 140 is configured to seal and or fill empty spaces in microstructures 30 of microfluidic device 10. Fluid sealant 140 may be configured to have additional functionality. From example, fluid sealant 140 (e.g., that includes Fluorinert™ FC-40) may be configured to enable delivery of oxygen to living cells that are included within sample fluid 110 that is trapped within chambers 60. (For example, a high electro-negativity of fluorine in FC-40 may enable high solubility of oxygen in fluid sealant 140.) Arrows 150 depict the flow of fluid sealant 140 through channels in microfluidic device 10. Fluid sealant 140 may flow in additional directions.

A fluorocarbon oil, for example FC-40 or HFE-7500, may contain perfluorocarbons (PFCs). The number of carbon atoms in a fluorocarbon molecule may help determine most physical properties of that fluorocarbon. The fluorocarbon oil may be chosen based on desired physical properties.

Fluorocarbons or other organofluorine compounds that contain only carbon and fluorine may be employed as fluid sealant 140. In some embodiments, fluid sealant 140 may include carbon and fluorine bonded together in strong carbon-fluorine bonds; the bonds may be single double bonds or triple bonds, the number of bonds relating to the stability and reactivity of the fluorocarbon.

Fluorocarbon oils may contain molecules that are not technically fluorocarbons but may be commonly referred to as fluorocarbons. Fluorocarbons may have high densities, in some embodiments up to over twice that of water. This high density may be due to their high molecular weight.

Fluorocarbon oils may have low intermolecular forces. The low intermolecular forces may provide for relatively low viscosities when compared to liquids of similar boiling point. Fluorocarbon oils may have relatively low surface tension, relatively low heats of vaporization, and relatively low refractive indices. Fluorocarbon oils may not be miscible with most organic solvents but are miscible with some hydrocarbons. Fluorocarbon oils may have very low solubility in water, and water may have a very low solubility in them.

FIG. 2E depicts is a schematic illustration of a step in the loading of a microfluidic device according to an embodiment of the invention.

FIG. 2E depicts a step in loading microfluidic device 10. After loading fluid sealant 140, fluid sealant 140 becomes interspersed throughout channels, microstructures 30 and chambers 60. In some embodiments of the invention, fluid sealant 140 becomes interspersed throughout a subset of structures, as described, for example, above, of microfluidic device 10. In some embodiments of the invention, vents 100 are filled with fluid sealant 140.

In some embodiments of the invention, fluid sealant 140 may be configured to seal the exit of chambers 60 such that sample fluid 110 or other fluids intended to be retained in chambers 60 are retained and isolated. Isolated sample fluid 110 may have limited opportunity to mix with or interact with reagents, or other fluids, in the environment outside of chambers 60 within microfluidic device 10, within the external (ambient) environment. Isolated sample fluid 110 may be isolated in chambers 60 wherein chambers 60 and vents 100 are sealed, or otherwise fully or partially plugged, by fluid sealant 140.

Once primary channel 90, secondary channel 80, microstructures 30 or a subset of microstructures 30, or vents 100 are filled with fluid sealant 140, sample fluid 110 may be confined or mostly limited to chambers 60. Little to no air may remain within microfluidic device 10.

FIG. 3A is a schematic illustration of the use of a pipette to load the microfluidic device according to an embodiment of the invention.

Microfluidic device 10 is be loaded with sample fluid 110 using a pipette 160. Microfluidic device 10 may be loaded with sample fluid 110 using other devices.

Sample fluid 110 is loaded into microfluidic device 10 at an inlet 180. For example, inlet 180 may represent a port or opening in cover 22 (FIG. 6B) enabling access to primary inlet 50.

A pressure difference (e.g., between an inlet and an outlet) that is applied to sample fluid 110 may be selected in accordance with the surface tension of sample fluid 110, and in accordance with properties of the surfaces that sample fluid 110 contacts within microfluidic device 10. In some embodiments, the pressure of sample fluid 110 as it is introduced into the microfluidic device is between 1.8 kilopascals (kPa) and 2.2 kPa, e.g., 2 kPa. In some embodiments the pressure of sample fluid 110 as it is introduced into the microfluidic device may be greater than 2.2 kPa. In some embodiments, the pressure of sample fluid 110 as it is introduced into the microfluidic device may be less than 1.8 kPa. For some conditions of surface tension and surface properties, the pressure difference between inlet and outlet may range from about 2 kPa to about 4 kPa.

Figure 3B:
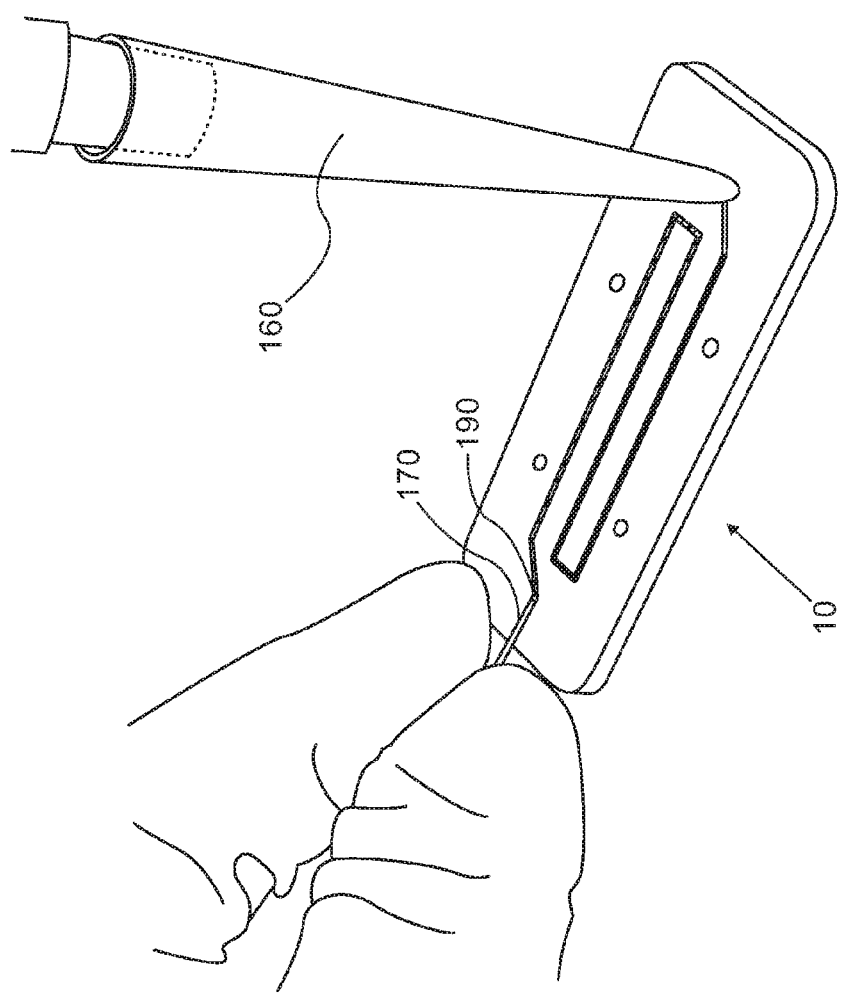
FIG. 3B is a schematic illustration of the use of a pipette to shear a sample loaded into a microfluidic device, according to an embodiment of the invention.

FIG. 3B is a schematic illustration of the use of a pipette to shear a sample loaded into a microfluidic device, according to an embodiment of the invention.

Sample fluid 110 in microfluidic device 10 may be sheared by the force of air introduced into the microfluidic device. Air may be introduced into inlet 180 using pipette 160. In some embodiments of the invention, shearing fluids, including, air or other propellants, may be used to shear sample 110. In some embodiments, the force of the air introduced as it is introduced into the microfluidic device is between 1.8 kPa and 2.2 kPa, e.g., 2 kPa. In some embodiments the pressure of air that is introduced into the microfluidic device may be greater than 2.2 kPa. In some embodiments, the pressure of air as it is introduced into the microfluidic device may be less than 1.8 kPa. For some conditions of surface tension and surface properties, the pressure difference between inlet and outlet may range from about 2 kPa to about 4 kPa.

While air is used to shear sample 110, a sponging device 170, e.g., filter paper or another absorbent material or object, may be used to extract or absorb expelled or extra fluid from microfluidic device 10. Sponging device is positioned at an outlet port 190. Outlet port 190 may represent a port or opening in cover 22 (FIG. 6B). Outlet port 190 may have a circular shape or another shape. The shape of outlet port 190 may be configured to facilitate sponging of residual liquid at outlet port 190.

Sponging device 170 may include Whatman paper, or another absorbent paper that may be grained, strong, or rigid. Whatman paper, or other absorbent materials may be cut into small ribbons to match the diameter of outlet port 190.

FIG. 3C is a schematic illustration of the use of a pipette to introduce a fluid sealant into a microfluidic device according to an embodiment of the invention.

Pipette 160 is used to introduce fluid sealant into microfluidic device 10. Fluid sealant may be introduced into various channels in microfluidic device 10 via one or a plurality of ports. Ports may include inlet 180. Ports may also include one or a plurality of side inlets 195. For example, Inlet 180 may represent a port or opening in a cover to enable access to primary inlet 50, may represent primary inlet 50, or may be distinct from primary inlet 50. Side inlets 195 may represent ports or openings in a cover to enable access to secondary inlets 40, may represent secondary inlets 40, or may be distinct from secondary inlets 40. In some embodiments of the invention, other devices or techniques may be used to introduce fluid sealant into microfluidic device 10.

FIG. 3C further depicts an enlarged view of a section of microfluidic device 10. A fluid sealant 140, as described above, is configured to fill primary channel 90, and maintain or isolate samples 110 or sheared samples 110 in chambers 60. Chambers 60 have walls 70. Vents 100 are located between, situated within, or in another relation to walls 70. Chambers 60 are indexed, including, in some embodiments, by an alphanumeric or symbolic index 185.

In some embodiments of the invention, walls 70 may be discrete and not connected to neighboring walls. In such a case, spaces between walls 70 may function as vents 100. Chambers may not be indexed. Chambers may be indexed using a variety of indexing methods.

Figure 4:
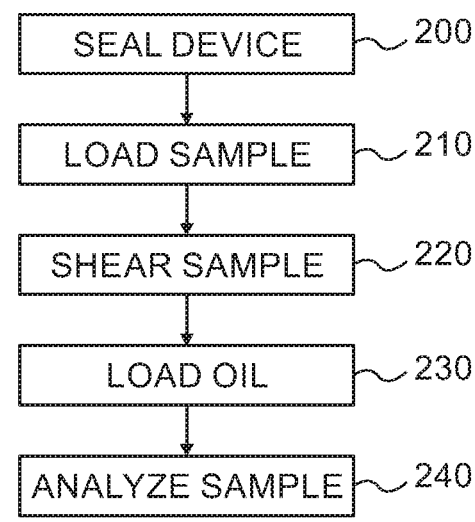
FIG. 4 is a schematic illustration of a method for introducing into and manipulating a sample in a microfluidic device, according to an embodiment of the invention.

FIG. 4 is a schematic illustration of a method for introducing into and manipulating a sample in a microfluidic device, according to an embodiment of the invention.

A microfluidic device may be prepared for use. Uses may include, but are not limited to, viewing or analyzing cell-to-cell signaling and interactions; viewing or analyzing cellular time responses of an individual cell to chemical stimulations and dose responses; viewing or analyzing bacterial strain resistance, screening against patterned multiple antibiotic drugs; viewing or analyzing prokaryotic single cell investigations in highly isolated environments; viewing or analyzing cellular uptake and excretion; conducting, viewing, or analyzing rapid tests of antibiotic susceptibility against different pathogen species; viewing or analyzing single cell secretion assays monitored over long incubation periods; conducting, viewing or analyzing single molecule PCR (by dilution, such that each droplet contains a single DNA molecule); conducting, viewing or analyzing RT-PCR performed on a single cell, immunoassays; or other uses.

As depicted as block 200, a microfluidic device is sealed by attachment of a substrate to a side of the device opposite the cover. In some embodiments of the invention, the substrate may be may be reversibly or irreversibly attached. A substrate may include glass, polylysine, poly-L-lysine treated glass, a tissue culture dish, a non-tissue-culture dish (polystyrene), PDMS, a Petri dish, a microscope slide, or another substrate. A substrate may be coated with a material to promote or inhibit adhesion of an analyte or analyte component, or to promote or inhibit cell growth.

In some embodiments of the invention, in attachment of the substrate, the microfluidic device may be placed on the surface such that no air bubbles are trapped between the microfluidic device and the substrate. In some embodiments of the invention, the microfluidic device, e.g., a surface of the microfluidic device wherein the structures of the microfluidic device are exposed to air, may be cleaned. In some embodiments, the surface may be cleaned with tape or other substances.

As depicted by block 210, a microfluidic device may be loaded with a fluid, for example, with an analyte or sample fluid, one or a plurality of reagents, a propellant, or another fluid.

In some embodiments of the invention, a primary inlet or additional secondary inlet may be used as an access port for loading fluids. For example, the port may include an opening in a cover of the microfluidic device. A pipette may be used to introduce the fluids into the access port. In some embodiments, once the fluid has been loaded into the access port, a device, e.g., a bulb from a pipette, may be used to push the fluid through the structures of the microfluidic device by gently squeezing the bulb until the fluid has been loaded. In some embodiments, the fluid may be fully loaded once it reaches an outlet port. Excess fluid may be sponged up using, for example, filter paper, such as Whatman filter paper. This step may be repeated with other fluids.

Box 220 depicts a step of shearing the fluid introduced in the step depicted by block 210. In some embodiments, a bulb of a pipette or another device may be used to inject air into a channel through an access port in the microfluidic device. Injection of the air (or another fluid) may result in removing fluid introduced into the microfluidic device from the channels of the device, thus separating the analyte or sample fluid into separate droplets. A filter paper or other absorbent device may be used to absorb any fluid that exits at an outlet port. The use of the filter paper to sponge up or absorb exiting fluid may prevent or inhibit back retraction of liquids into or within the microfluidic device. In some embodiments, all excess or exiting fluid may be absorbed in preparation for a following step.

Box 230 depicts a step of loading a fluid sealant, e.g., a hydrophobic fluid such as an oil. In some embodiments of the invention, a fluorocarbon oil may be loaded into the microfluidic device. In some embodiments, the oil may be loaded into an inlet that leads to a primary channel in the microfluidic device. Oil may be loaded into additional inlets, for example on the sides of the microfluidic device to introduce the oil into one or a plurality of side channels. Openings or inlets may be sealed after the fluid sealant is loaded, or at any other point during a loading process.

In some embodiments, capillary forces may draw the inserted oil into primary and side channels, in addition to other spaces within the structures of the microfluidic device.

Box 240 depicts a step wherein the fluid or components of the fluid inside the microfluidic device may be analyzed. For example, an analysis may be made through a substrate (e.g., microscopic examination) or after removal of the substrate.

Figure 5:
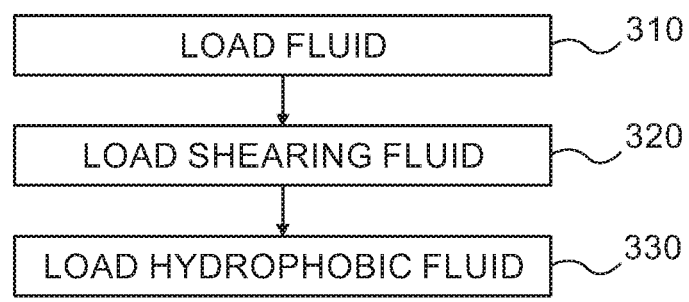
FIG. 5 is a schematic illustration of a method for employing a microfluidic device, according to an embodiment of the invention.

FIG. 5 is a schematic illustration of a method for employing a microfluidic device according to an embodiment of the invention.

A substrate may be attached to the microfluidic device prior to use. In some embodiments, the substrate may be attached in preparation for introducing fluids, including, for example, samples or oils, into the microfluidic device. Attachment of the substrate may be reversible. Reversible attachment may enable access to or extraction of a sample from a chamber of the microfluidic device.

Box 310 represents loading of at least one fluid into the microfluidic device. The loaded fluid may be a sample fluid or a sample fluid containing analyte. In some embodiments, the fluid is introduced through a port into a primary channel of the microfluidic device. In some embodiments of the invention, fluids may be introduced into the microfluidic device via one or a plurality of channels.

Box 320 depicts the use of a shearing flow. In some embodiments of the invention, the shearing flow may evacuate the primary channel in the microfluidic device. Shearing may be accomplished by introducing a shearing fluid (typically a gas) that applies a shearing force on fluid that was previously loaded into the microfluidic device. The shearing may result in the sample fluid being divided or apportioned into droplets of the sample fluid.

In some embodiments, the introduction of fluids prior to shearing may result in a gradient of concentration of the resulting droplets after shearing. In some embodiments, the microfluidic device and the sample or other fluids may be configured to provide a particular concentration of sample in each of a plurality of chambers in the microfluidic device. A droplet of sample fluid may be retained or stabilized in a chamber by one or a plurality of design characteristics. Stabilizing design characteristics or factors may include the geometry of the chamber (e.g., a rectangular shape of the chamber), a composition, texture, or other characteristic of a surface of the chamber, or other factors. The factors may lead to surface energy minimization of the droplets or the material composition (e.g., of PDMS) of the device or of a portion thereof, e.g., of the chambers. Liquid surface tension or liquid-device interfacial tension may lead to stabilization of the droplets within the chambers.

In some embodiments of the invention, properties of an inlet via which a sample fluid may be introduced into the microfluidic device may facilitate the creation of a concentration gradient throughout the device. Properties of the inlet may include a geometry of the inlet, a depth of the inlet, a diameter of the inlet, a circumference of the inlet, or other factors related to the inlet.

In some embodiments of the invention, the interfacial tension of the chamber, and in some examples the PDMS and or other materials in the composition of the chamber, may provide or may facilitate the stabilization or retention of a sample within the chamber. In some examples, this stabilization may occur prior to shearing of the sample.

Box 330 depicts introduction of a hydrophobic fluid that functions as a fluid sealant. In some embodiments of the invention, the hydrophobic fluid may be an oil. In some embodiments of the invention, creation of an immiscible phase between the hydrophobic fluid and the sample fluid is configured to create discrete isolated volumes of the sample fluid within the microfluidic device. The isolated volumes may enable application of discrete or digital microfluidics, or the creation of discrete microreactors containing sample. The hydrophobic fluid may be configured to push the sample into the chambers and to seal any spaces or voids between chambers.

Figure 6A:
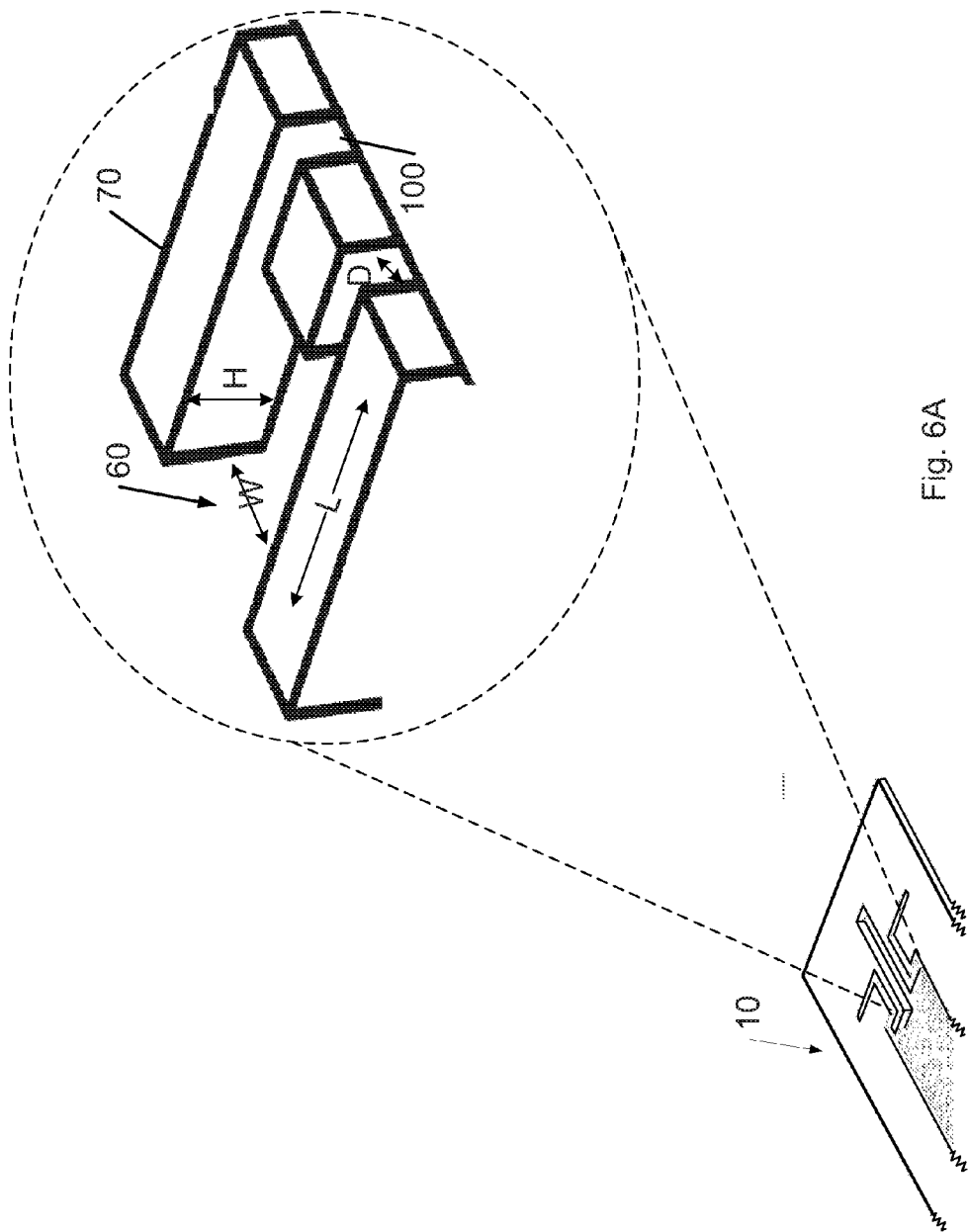
FIG. 6A depicts a schematic view of an individual chamber, according to an embodiment of the invention; and, FIG. 6B is a schematic illustration of a cut out of a portion of a microfluidic device, according to an embodiment of the invention.
Figure 6B:
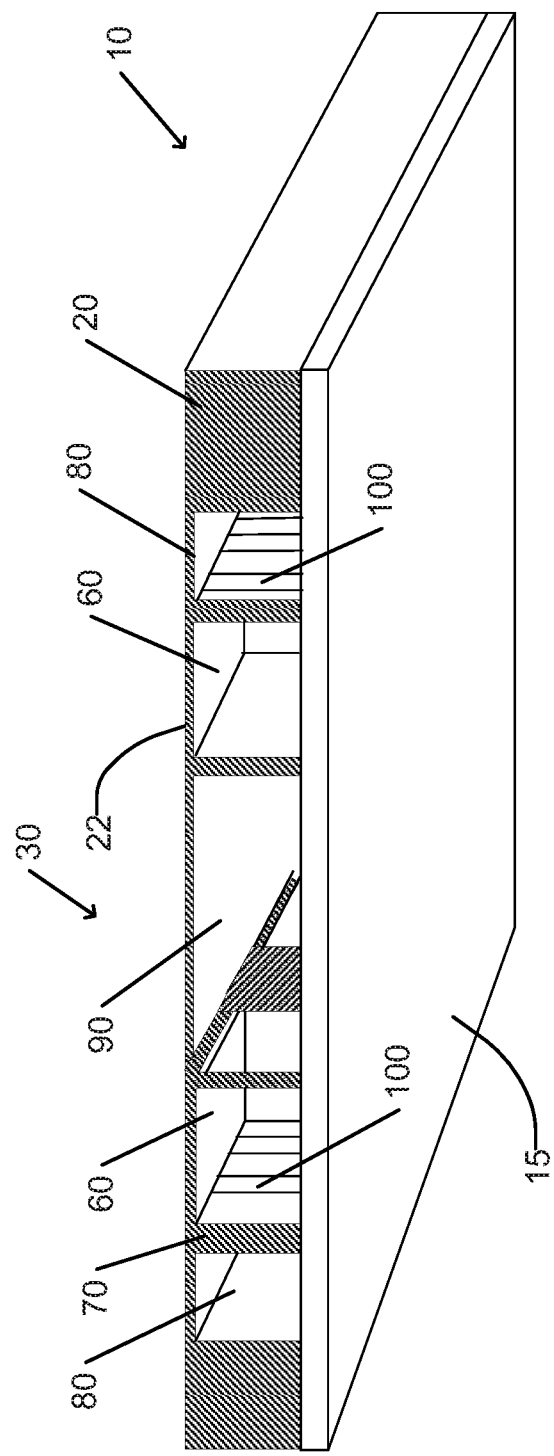
FIG. 6C is a schematic cross section illustration through a primary channel of a microfluidic device, according to an embodiment of the invention.

FIG. 6A depicts a schematic view of an individual chamber, according to an embodiment of the invention. In some embodiments, the structure and geometry of a chamber 60 within a microfluidic device 10, as depicted herein in the enlargement, may facilitate the generation of droplets from a sample fluid directly inside one or a plurality of chambers 60.

A process of forming a droplet within chamber 60 may be executed in two steps. In some embodiments, the process of generating a droplet within chamber 60 may be executed in one step. In some embodiments of the invention, the process of generating a droplet within chamber 60 may be executed in more than two steps.

Initially a fluid, e.g., a sample fluid as described above, may be injected by pressure into a primary channel and chambers 60 through an inlet. The method of injection, and the channel and chambers, may be, for example, as described above.

Vents 100 within chambers 60 may allow air to escape from chambers 60, and, in some examples, from microfluidic device 10, through another channel, e.g., the secondary channel or evacuation channel as described above.

Vents 100 may also act as a surface tension barrier which may limit a fluid from further flowing into the secondary channel.

A second step during droplet generation may involve shearing the continuous fluid into separate droplets, for example, as described above.

In some embodiments of the invention, stabilized stationary droplets may be surrounded by air and walls of the chamber 60, walls 70 for example, as described above. After shearing, the droplets of the sample fluid may be sheathed by oil, e.g., the fluorocarbon oil described above, or by another fluid sealant. The sheathing of the droplets by the fluorocarbon oil may limit rapid evaporation of the sheared droplets within the chambers.

The fluid sealant may be injected into microfluidic device 10 from an inlet. In some embodiments of the invention, the fluid sealant may be injected or otherwise provided into microfluidic device 10 from more than one inlet. In some examples, the fluid sealant may be injected into microfluidic device 10 via three inlets. The three inlets may include an inlet into the primary channel and an inlet into each of at least two secondary channels.

The fluid sealant may flow via capillary force and surround the droplets in chambers 60 without forming trapped air bubbles. The materials comprising microfluidic device 10, e.g., PDMS, may facilitate the flow via capillary force of the fluid sealant through the microfluidic device.

In some embodiments of the invention, the shearing step may rely on surface energy minimization considerations. For example, the surface energy may as described by:

$$E = \gamma_{LG} \cdot S_{LG} + \gamma_{SL} \cdot S_{SL},$$

where E represents the energy of a system; $\gamma_{LG}$ represents the liquid-air surface tension; $\gamma_{SL}$ represents the surface liquid interfacial tension; $S_{LG}$ is a value that represents the area wherein the fluid is in contact with air; and $S_{SL}$ represents the area wherein the fluid is in contact with a material from which the microfluidic device is made, e.g., PDMS.

The energy required to split a sessile electrowetting on dielectrics (EWOD) droplet may be reduced when a droplet is squeezed between two parallel surfaces. In these instances, the system's interfacial energy change may be represented by $$\frac{\Delta E}{E} = \frac{\sqrt{2}-1}{1 + \frac{\gamma_{SL}\alpha}{\gamma_{LG}\delta}},$$

where $\alpha$ is the droplet in-plane radius; and $\delta$ is the parallel plate separation.

For cases where $\gamma_{LG}\delta \ll \gamma_{SL}\alpha$ this expression reduces to:

$$\frac{\Delta E}{E} \sim \frac{\gamma_{LG}\delta}{\gamma_{SL}\alpha}.$$

Minimizing a fluid-air interface may reduce an energy barrier for droplet shearing and the eventual splitting of the sheared fluid into droplets.

As depicted in the figure, a chamber 60 within microfluidic device 10 may stabilize a droplet of fluid by surrounding the droplet with four surfaces. Chambers 60 within microfluidic device 10 may be configured to provide a larger fluid to surface ratio.

This larger fluid to surface ratio may favor the splitting of the droplet via shearing over the drainage of the droplet as a result of the shearing.

In some embodiments of the invention, for a specific droplet volume, chamber geometry may include an elongated and flat geometry, for example, when W≪L and H≪L.

An elongated and flat chamber may, in some examples, limit the complete filling of the chamber with sample fluid or droplets. In some embodiments of the invention, a flat chamber may require larger pressures to be applied within the shearing process. These larger pressures may lead to the failure of the vents to prevent the escape of fluid or droplets from chambers.

In some embodiments of the invention chamber dimensions may be as indicated by W, L, and H wherein, W may be between 50 µm and 350 µm, e.g., 200 µm; L may be between 100 µm and 700 µm, e.g., 400 µm; and H may be between 50 µm and 300 µm, e.g., 120 µm.

In some embodiments of the invention, D, e.g., the width of a vent 100, may be 4 µm to 8 µm, e.g., 6 µm. Width in such a range may result in reduction of sensitivity of vent 100 to fluid pressure from the injection or shearing steps. This reduced sensitivity to pressure may result from static surface tension characteristics, rather than from kinetic properties or liquid bulk flow properties of the fluids.

In some embodiments of the invention, D may be configured to be between 4 µm and 8 µm, e.g., 6 µm, to allow for manual loading of microfluidic device 10, for example by applying pressure with a bulb or a pipette.

In some embodiments of the invention, sample fluid loading and sample fluid shearing may be performed in a single step. For example, by adjusting the volume of a sample fluid that is introduced into microfluidic device 10 to match a single droplet volume multiplied by the total number of desired droplets within the device, the fluid may be segmented into the desired number of chambers 60.

Figure 6C:
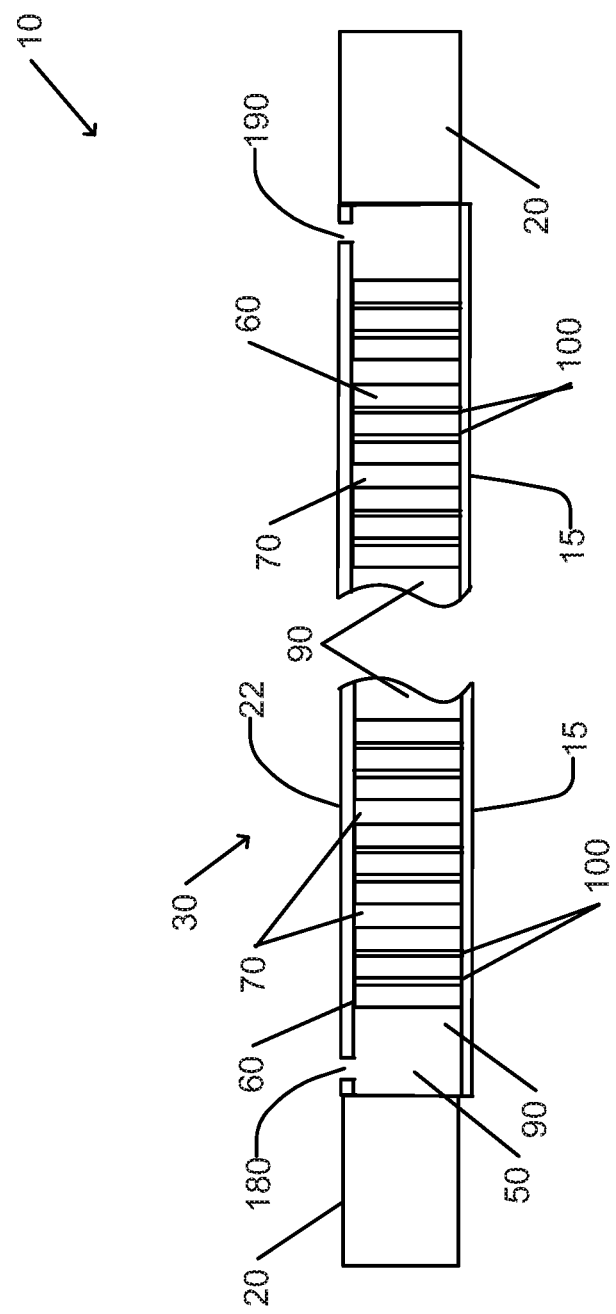

FIG. 6B is a schematic illustration of a cut out of a portion of a microfluidic device, according to an embodiment of the invention. FIG. 6C is a schematic cross section illustration through a primary channel of a microfluidic device, according to an embodiment of the invention.

FIG. 6B depicts a cutout section of microfluidic device 10. Microfluidic device 10 includes primary channel 90, a plurality of chambers 60, the chambers 60 located between a secondary channel 80 and a primary channel 90.

FIG. 6C depicts end sections of primary channel 90, and structure that may be visible from primary channel 90.

FIGS. 6B and 6C are not necessarily drawn to scale, nor are the relative sizes, positions, and geometries of the components and items in FIGS. 6B and 6C necessarily accurate or consistent with one another or with others of the Figures.

Chambers 60 are partially bounded by walls 70. Walls 70 include a plurality of vents 100. Vents 100 are configured to allow the flow of some fluids below a threshold viscosity through the vent and into secondary channel 80. Vents 100 may be configured to isolate, contain, or otherwise maintain a sample fluid, analyte or other fluid within chamber 60. The fluid contained within chamber 60 may have a viscosity greater than a predetermined viscosity threshold.

Cover 22 includes inlet 180 in the form of an opening in cover 22 that connects primary inlet 50 to the outside of microfluidic device 10. Similarly, outlet port 190 is in the form of an opening that connects an end of primary channel 90 to the outside. Substrate 15 covers microstructures 30 such that a fluid content of primary channel 90 or of a chamber 60 may contact substrate 15 (e.g., when microfluidic device is oriented as shown, with substrate 15 at the bottom, such that gravity assists in maintaining contact between the fluid and substrate 15).

Fluids within microfluidic device 10 may act as Newtonian fluids wherein each fluid has a constant viscosity, or its reciprocal value, fluidity, at a given temperature. A fluid (e.g., air) with a low viscosity may rapidly pass through vents 100, thus enabling a sample fluid to freely enter a chamber 60 (The viscosity of air is about 20 µPa·s or less at typical ambient (e.g., room) temperatures and pressures.) On the other hand, a fluid (e.g., a liquid) with relatively large surface tension may be prevented by the narrowness of vents 100 from passing through vents 100.

In some embodiments of the invention, the sample fluid, and in some examples, a sample fluid containing an analyte, may have a surface tension that is greater than a predetermined threshold and is thus inhibited or prevented from passage through vents 100.

In some embodiments of the invention, the microfluidic device may be configured (e.g., by selection of surface properties of a substrate 15) such that the surface tension threshold for passage through vents 100 is less than a surface tension of the sample fluid.

Chambers 60, primary channel 90, secondary channel 80 and other microstructures 30, or additional components of microfluidic device 10 may be sealed against an outside environment by a seal, for example, substrate 15, as described above.

In some embodiments of the invention, a microfluidic device reversibly sealed against an outside environment may be recycled, reused, or otherwise repurposed. In some embodiments of the invention, a microfluidic device is reversibly sealed against an outside environment may be reversibly sealed such that the seal is watertight. In some embodiments of the invention, a microfluidic device reversibly sealed against an outside environment such that the seal can be relatively easily removed from microfluidic device, and the device cleaned or analyzed. In some embodiments of the invention, a microfluidic device is reversibly sealed against an outside environment such that the seal cannot be easily removed from microfluidic device, Embodiments of the present invention may include apparatuses for performing the operations described herein. Such apparatuses may be specially constructed for the desired purposes, or may comprise computers or processors selectively activated or reconfigured by a computer program stored in the computers. Such computer programs may be stored in a computer-readable or processor-readable non-transitory storage medium, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions. It will be appreciated that a variety of programming languages may be used to implement the teachings of the invention as described herein. Embodiments of the invention may include an article such as a non-transitory computer or processor readable non-transitory storage medium, such as for example, a memory, a disk drive, or a USB flash memory encoding, including or storing instructions, e.g., computer-executable instructions, which when executed by a processor or controller, cause the processor or controller to carry out methods disclosed herein. The instructions may cause the processor or controller to execute processes that carry out methods disclosed herein.

The invention claimed is:

1. A microfluidic device comprising a platform with a microstructure including a primary channel and a plurality of chambers that open to the primary channel to enable a sample fluid that is loaded into the device via the primary channel to flow into said plurality of chambers, each chamber of said plurality of chambers having a volume that is less than 100 nanoliters and being connected by a vent to a secondary channel of the microstructure, wherein the vent comprises one or a plurality of slits sufficiently narrow to enable a gas to escape from the chamber to the secondary channel while inhibiting flow of the sample fluid from the chamber through the vent outward through the one or a plurality of slits into the secondary channel.

2. The device of claim 1, wherein each chamber of said plurality of chambers is connected to the secondary channel by one or a plurality of additional vents.

3. The device of claim 1, wherein the platform is formed such that one face of the microstructure is covered by a cover that includes an opening to enable fluid flow into or out of the primary channel or the secondary channel via the cover.

4. The device of claim 1, wherein the platform is formed such that one face of the microstructure is exposed allowing attachment of a substrate to cover the exposed face of the microstructure.

5. The device of claim 4, wherein the substrate is removable after attachment to the microstructure.

6. The device of claim 4, wherein the substrate comprises glass, plastic, or an elastomer.

7. The device of claim 1, wherein said plurality of chambers comprises between 100 and 1000 chambers.

8. The device of claim 1, wherein each chamber of said plurality of chambers is configured to retain a droplet of the sample fluid within that chamber when the sample fluid is removed from the primary channel.

9. The device of claim 1, wherein each of said plurality of chambers is labeled with an indexing identification number or a designation.

10. A method for storing droplets of a sample fluid, the method comprising:
   introducing the sample fluid via a primary channel of a microstructure into a plurality of chambers of the microstructure that are open to the primary channel, each chamber of said plurality of chambers having a volume that is less than 100 nanoliters and being connected by a vent to a secondary channel of the microstructure, wherein the vent comprises one or a plurality of slits sufficiently narrow to enable a gas to escape from the chamber to the secondary channel while inhibiting flow of the sample fluid from the chamber through the vent outward through the one or a plurality of slits into the secondary channel;
   introducing a shearing fluid into the primary channel to remove the sample fluid from the primary channel while a droplet of the sample fluid is retained within each chamber of said plurality of chambers; and
   introducing a fluid sealant into the primary channel and into the secondary channel to isolate the droplet in one chamber of said plurality of chambers from a droplet in another chamber of said plurality of chambers and from an ambient environment.

11. The method of claim 10, wherein introducing the sample fluid, the shearing fluid, or the fluid sealant comprises introducing the sample fluid, the shearing fluid, or the fluid sealant via an opening in a cover that covers a face of the microstructure.

12. The method of claim 10, the gas or the evacuated sample fluid is removed from the microstructure via an opening in a cover that covers a face of the microstructure.

13. The method of claim 10, further comprising attaching a substrate to an exposed face of the microstructure so as to cover that side of the microstructure.

14. The method of claim 13, further comprising removing the attached substrate to enable access to contents of the microstructure.

15. The method of claim 14, wherein the access comprises analysis of the droplet in a chamber of said plurality of chambers or removal of the contents from the microstructure.

16. The method of claim 10, wherein the fluid sealant comprises a hydrophobic fluid.

17. The method of claim 16, wherein the hydrophobic fluid comprises a fluorocarbon oil.

18. The method of claim 10, wherein introducing the sample fluid comprises introducing two different sample fluids via different ends of the primary channel to generate a chemical concentration gradient within the primary channel.

19. The method of claim 18, wherein the droplet retained in one chamber of said plurality of chambers is characterized by a chemical concentration that is different from the chemical concentration that characterizes a droplet retained in another chamber of said plurality of chambers.

\* \* \* \* \*